United States Patent
Kim et al.

(10) Patent No.: US 7,978,075 B2
(45) Date of Patent: Jul. 12, 2011

(54) APPARATUS AND A METHOD FOR RECOGNIZING AN ACTIVITY OF DAILY LIVING

(75) Inventors: Ig Jae Kim, Seoul (KR); Hyoung Gon Kim, Seoul (KR); Sang Chul Ahn, Seoul (KR)

(73) Assignees: Korea Institute of Science and Technology, Seoul (KR); Electronics and Telecommunications Research Institute, Daejeon (KR)

( * ) Notice: Subject to any disclaimer, the term of this patent is extended or adjusted under 35 U.S.C. 154(b) by 309 days.

(21) Appl. No.: 12/134,480

(22) Filed: Jun. 6, 2008

(65) Prior Publication Data
US 2009/0179739 A1   Jul. 16, 2009

(30) Foreign Application Priority Data
Jan. 14, 2008  (KR) ............... 10-2008-0003977

(51) Int. Cl.
G08B 13/14 (2006.01)
G08B 21/00 (2006.01)
G09B 21/00 (2006.01)
G09B 9/00 (2006.01)
A63B 69/00 (2006.01)

(52) U.S. Cl. ............... 340/572.1; 340/669; 340/825.19; 434/247

(58) Field of Classification Search .... 340/572.1–572.9, 340/568.1, 825.19, 669, 573.1, 539.11, 539.12, 340/689, 10.1; 600/595; 434/247, 251, 252, 434/253, 256; 601/23
See application file for complete search history.

(56) References Cited

U.S. PATENT DOCUMENTS

| | | | |
|---|---|---|---|
| 6,511,443 B2 * | 1/2003 | Cuce' et al. | 600/595 |
| 6,522,266 B1 * | 2/2003 | Soehren et al. | 340/988 |
| 6,624,752 B2 * | 9/2003 | Klitsgaard et al. | 340/572.1 |
| 6,747,560 B2 * | 6/2004 | Stevens, III | 340/572.4 |
| 7,602,301 B1 * | 10/2009 | Stirling et al. | 340/573.1 |
| 7,714,728 B2 * | 5/2010 | Koblasz | 340/573.1 |
| 2005/0131736 A1 | 6/2005 | Nelson et al. | |
| 2005/0184870 A1 * | 8/2005 | Galperin et al. | 340/568.2 |
| 2005/0234309 A1 * | 10/2005 | Klapper | 600/300 |
| 2006/0220882 A1 * | 10/2006 | Makino | 340/573.1 |
| 2007/0018826 A1 * | 1/2007 | Nowak et al. | 340/572.1 |
| 2007/0135264 A1 * | 6/2007 | Rosenberg | 482/8 |
| 2007/0182578 A1 | 8/2007 | Smith | |
| 2008/0088472 A1 * | 4/2008 | Beale | 340/825.19 |
| 2009/0135009 A1 * | 5/2009 | Little et al. | 340/540 |
| 2009/0160620 A1 * | 6/2009 | August et al. | 340/10.3 |
| 2010/0007512 A1 * | 1/2010 | Ghovanloo et al. | 340/825.19 |

* cited by examiner

Primary Examiner — Jennifer Mehmood
(74) Attorney, Agent, or Firm — Fenwick & West LLP

(57) ABSTRACT

Provided is an apparatus for recognizing an activity of daily living (ADL). The apparatus includes a radio frequency identification (RFID) reader for reading the information of an RFID tag to recognize a motion object, a motion detector attached on a moving subject for acquiring acceleration information and recognizing a motion characteristic, and a controller for receiving information on the motion object from the RFID reader and information on the motion characteristic from the motion detector and then recognizing an ADL.

5 Claims, 5 Drawing Sheets

APPARATUS AND A METHOD FOR RECOGNIZING AN ACTIVITY OF DAILY LIVING

CROSS-REFERENCE TO RELATED APPLICATION

This application claims priority under 35 U.S.C. §119(a) from Republic of Korea Patent Application No. 10-2008-0003977, filed on Jan. 14, 2008, which is incorporated by reference herein in its entirety.

BACKGROUND OF THE INVENTION

1. Field of the Invention

The following description relates to an apparatus and a method for recognizing an activity of daily living (ADL), and more specifically to an apparatus and a method for recognizing an ADL, which automatically and accurately recognizing an ADL.

2. Description of the Related Art

Activities of daily living are the things we normally do in daily living including any daily activity we perform for self-care, work, homemaking, and leisure. Health professionals routinely refer to the ability or inability to perform ADL as a measurement of the functional status of a person. This measurement is useful for assessing the elderly, the mentally ill, those with chronic diseases, and others, in order to evaluate what type of health care services an individual may need.

Activities of daily living include transferring from bed to chair, and back, eating, dressing and undressing, walking and using instruments with hands. Activities of daily living include instrumental activities of daily living.

ADL is used in a medical treatment field so as to measure how much the elderly need the help from others. ADL may include the following general activities—bathing, dressing, using the toilet, transferring, maintaining continence, eating, and face washing. And ADL may include the following instrumental activities—make-up, housework, meal preparation, laundry, using transportation, managing money, using the telephone, shopping, community mobility, and taking medications, for example.

To measure ADL, the motion of a moving subject should be accurately recognized. In the case of an instrumental activity, the object of the instrumental activity should be accurately recognized. Depending on the state of the moving subject, the motion is varied in various manners. Therefore, there are difficulties in accurately recognizing ADL.

SUMMARY OF THE INVENTION

An advantage of the present invention is that it provides an apparatus and a method for recognizing ADL, which can accurately recognize the motion of a moving subject and accurately recognize an object of an instrumental activity.

According to an aspect of the invention, an apparatus for recognizing activity of daily living (ADL) includes a radio frequency identification (RFID) reader for reading the information of an RFID tag to recognize a motion object, a motion detector attached on a moving subject for acquiring acceleration information and recognizing a motion characteristic, and a controller for receiving information on the motion object from the RFID reader and information on the motion characteristic from the motion detector and then recognizing an ADL.

Preferably, the RFID tag is attached on the motion object.

Preferably, the controller recognizes the motion type of the moving subject based on the motion characteristic information received from the motion detector, and then recognizes the motion object based on the motion object information received from the RFID reader, thereby recognizing the ADL.

Preferably, the controller classifies the motion characteristic information received from the motion detector, into predetermined motion type classes, and recognizes the ADL only when the relationship between the classified motion type classes and the motion object information received from the RFID reader is established.

Preferably, the motion type classes include an up-and-down motion, a down-and-up motion, a left-and-right motion, a right-and-left motion, a front-and-back motion, a back-and-front motion and a rotational motion.

Preferably, the controller recognizes the motion object based on the motion object information received from the RFID reader, and then recognizes a motion type only when the motion coincides with an essential behavior of the recognized motion object, thereby recognizing the ADL.

According to another embodiment of the invention, a method for recognizing an activity of daily living (ADL) is provided, the method comprising the steps of recognizing a characteristic of a motion by acquiring acceleration information for the motion of a moving subject, recognizing a motion object by reading the information of an RFID tag, and recognizing an ADL by receiving information on the recognized motion characteristic and information on the recognized motion object.

Preferably, recognizing the motion characteristic includes the steps of recognizing the current state of the body of the moving subject based on the motion characteristic information for the lower part of the body, and recognizing a detailed motion characteristic based on the motion characteristic information for the upper part of the body of the moving subject.

Preferably, recognizing the ADL includes the steps of classifying the received motion characteristic information into predetermined motion type classes, and recognizing the motion characteristic information as the ADL only when the relationship between the classified motion type classes and the received motion object information is established.

Preferably, the motion type classes include an up-and-down motion, a down-and-up motion, a left-and-right motion, a right-and-left motion, a front-and-back motion, a back-and-front motion, and a rotational motion.

According to a further aspect of the invention, a method for recognizing an activity of daily living (ADL) is provided, the method comprising the steps of recognizing a motion object by reading the information of an RFID tag, acquiring a motion characteristic information of a moving subject only when a motion coincides with an essential behavior of the recognized object, and recognizing an ADL by receiving information on the recognized motion characteristic and information on the recognized motion object.

BRIEF DESCRIPTION OF THE DRAWINGS

The accompanying drawings, which are included to provide a further understanding of the implementations and are incorporated in and constitute a part of this disclosure, illustrate implementation(s) and together with the description serve to explain the implementation(s).

DETAILED DESCRIPTION OF THE EMBODIMENTS

Hereinafter, an apparatus and a method for recognizing ADL according to an embodiment of the present invention will be described with reference to the accompanying drawings.

Figure 1:
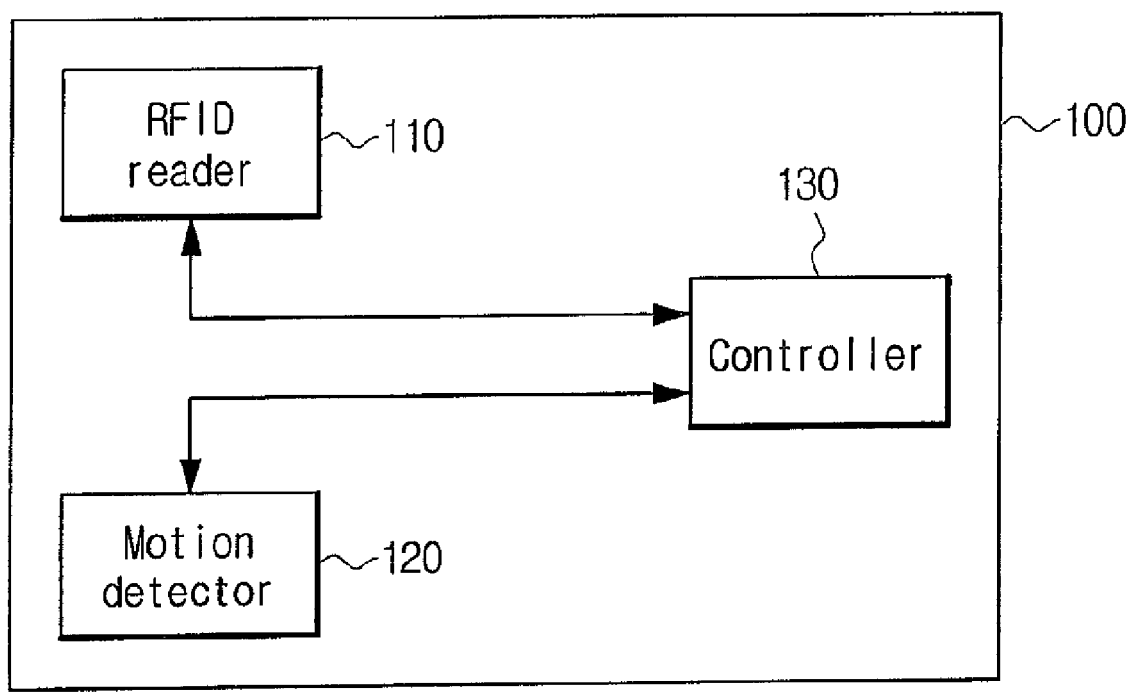
FIG. 1 is a block diagram showing the configuration of an apparatus for recognizing ADL according to an embodiment of the invention.

FIG. 1 is a block diagram showing the configuration of an apparatus for recognizing ADL according to an embodiment of the invention. As shown in FIG. 1, the apparatus 100 for recognizing ADL includes an RFID (radio frequency identification) reader 110 which reads the information of a tag to recognize a motion object, a motion detector 120 which is attached on a moving subject and acquires acceleration information to recognize a motion characteristic, and a controller 130 which receives information on the motion object from the RFID reader 110 and information on the motion characteristic from the motion detector 120, thereby recognizing ADL.

The apparatus 100 recognizes ADL based on the motion object information read by the RFID reader 110 and the motion characteristic recognized by the motion detector 120.

At least one motion detector 120 is attached to a predetermined portion of the moving subject so as to recognize a motion characteristic. An example of the motion detector 120 is a three-axis acceleration sensor. Now, a process of acquiring motion characteristic information by using the three-axis acceleration sensor, which is an example of the motion detector 120, will be described. The process of acquiring motion characteristic information by using the three-axis acceleration sensor is only an example and the motion characteristic information may be acquired by another method.

To recognize the motion of the moving subject, learning data acquisition is required. The three-axis acceleration sensors may be attached on the wrist, the waist, and the thigh of a user to collect motion data.

Then, the acceleration data acquired by the three-axis acceleration sensors are fast-Fourier-transformed (FFT) within a 256-sample window (four seconds), and the mean, energy, and correlation for each of X, Y, and Z axes are calculated on the basis of the fast-Fourier-transformed data. As a result, 12 feature values (MeanX, MeanY, MeanZ, EnergyX, EnergyY, EnergyZ, EntropyX, EntropyY, EntropyZ, CorrelationXY, CorrelationYZ, and CorrelationXZ) for each sensor are generated. The window is moved in such a manner that 128 samples are overlapped. Then, a new feature is calculated at every two seconds.

The respective feature values are calculated as follows.

The mean corresponds to a mean acceleration value of the window.

To calculate the energy, magnitudes excluding DC components are squared. Then, the squared magnitudes are summed. The summed value (Σ(Magnitude)) is divided by the window length and is then normalized to calculate the energy.

The entropy can be calculated using normalized information entropy of magnitudes excluding DC components.

The information entropy can be calculated by Equation 1.

$$-\sum_{i=1}^{n} p(x_i)\log_2 P(x_i)$$ [Equation 1]

The probability value can be calculated by the following process. First, the distribution range of magnitudes is divided into predetermined intervals. Then, the number of magnitudes belonging to each interval is counted to calculate the probability value.

To calculate the correlation, the inner products (X-axis·Y-axis, X-axis·Z-axis, and X-axis·Z-axis) of the respective axes are calculated, and are then divided by the window length.

Using the feature vectors extracted in such a manner, the motion characteristic can be judged. For example, a decision tree algorithm can be used to recognize ADL.

The RFID detector 110 serves to recognize a motion object, that is, object information. As the RFID 110 reads the information of a tag attached to the object, the RFID 110 recognizes the motion object.

Figure 2A:
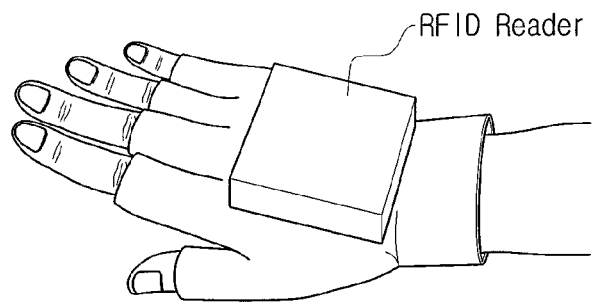
FIGS. 2A and 2B show an example of an RFID Reader and an RFID Tag, respectively.
Figure 2B:
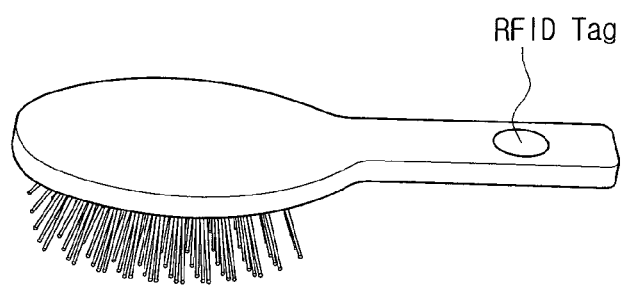

The RFID technique is an automatic identification method used to read product information included in an RFID tag by using an RFID reader connected to an antenna, instead of an existing barcode which is attached on a product to inform the information of the product. Researches on the automatic identification technique required by the next-generation network and the network technology using the automatic identification technique are being actively conducted. In the present invention, the RFID system is used as a system for recognizing an object which is handled by a user. The system can be implemented in an accurate and simple manner and serves to recognize a motion object. The RFID system can perform short-distance recognition and middle-to-long-distance recognition. In the present invention, to recognize an object which is held by a user, an RFID reader with a frequency band of 13.56 MHz may be used, which recognizes only a tag within a distance of 5 cm. FIG. 2A shows an example of the RFID Reader and FIG. 2B shows an example of the RFID Tag. And FIG. 3 shows an example of the RFID system.

Referring to FIG. 2A, an RFID reader is attached to the human body. For convenience of use, the RFID reader may be manufactured in the form of glove.

Referring to FIG. 2B, an RFID tag is attached to a motion object. The RFID tag may be manufactured in such a shape that it can be easily attached to an object.

Figure 3:
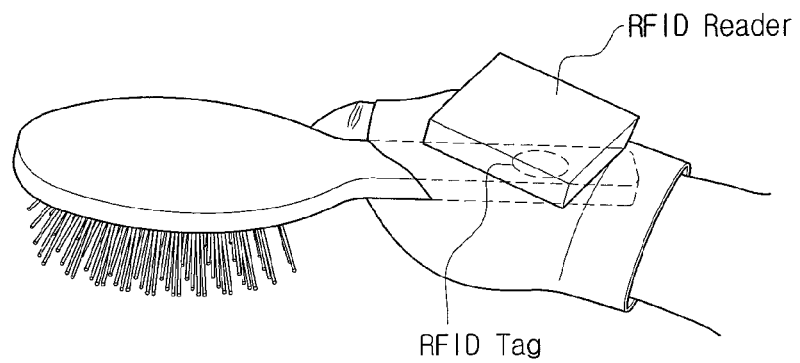
FIG. 3 shows an example of an RFID system.

Referring to FIG. 3, the RFID reader attached to the human body reads identification information from the RFID tag attached to the object so as to recognize the object.

The controller 130 receives the motion object information from the RFID reader 110 and motion characteristic information from the motion detector 120, thereby recognizing ADL.

The operation of the controller to control the recognizing of ADL based on the motion characteristic information and the subject information can be implemented in various manners.

The controller 130 recognizes the motion type of the moving subject based on the motion characteristic information received from the motion detector 120, and then recognizes the motion object based on the motion object information received from the RFID reader 110, thereby recognizing ADL. That is, after the motion type of the moving subject is recognized, the motion object information is recognized so as to recognize ADL.

At this time, the controller 130 classifies the motion characteristic information, received from the motion detector 120, into predetermined motion type classes. Only when the relationship between the classified motion type classes and the motion object information received from the RFID reader 110 is established, the motion characteristic information can be classified as an ADL.

As for motions classified into the predetermined classes, an up-and-down motion, a down-and-up motion, a left-and-right motion, a right-and-left motion, a front-and-back motion, a back-and-front motion, and a rotational motion are exemplified. When the type of the motion is recognized, the motion object information is recognized. In this case, when the relationship is established, the motion can be classified as an ADL.

For example, the motion information on the lower part of the body is read from two acceleration sensors (attached to the waist and the thigh) among the three acceleration sensors, and the current state of the user is discriminated through a decision tree method. For example, it is judged whether the moving subject stands, lies, sits, walks, or runs.

Further, the motion information of the hand, received from the acceleration sensor worn around the wrist, is discriminated through the decision tree method and is then combined with the object information read by the RFID reader 110 so as to finally determine the ADL.

The information read from the RFID reader 110 is an accurate value with no error. Therefore, when the RFID reader is used, it can be considered that an error does not occur practically. However, although the object is recognized by the RFID reader 110, it should be discriminated whether the user holds the object to utilize the essential property of the object or the object is just recognized, in order to accurately infer the activity of the user. Therefore, in the present invention, it is checked whether or not the particular object is continuously recognized by the RFID reader 110 at the same time as the motion information extraction time. Further, an instrumental activity is extracted by judging whether or not the hand of the user moves in a state where the object is recognized by the RFID reader 110. Through this process, false positive errors can be reduced. Therefore, the state of the user is estimated by the motion of the lower part of the body. In this state, it is finally determined what motion the user is taking. In such a system, the activity and the state are judged independently. Therefore, when a person takes a certain behavior, the motion and the state of the person can be judged, even though data including a specific state and behavior is not input. This means that combing the hair while sitting, combing the hair while standing, and so on can be classified differently. Further, since the range of recognizable objects can be sufficiently expanded, the number of activities which can be classified may increase.

After recognizing the motion object based on the motion object information input from the RFID reader 110, the controller 130 recognizes a motion type only when the motion coincides with an essential behavior of the recognized motion object, thereby recognizing ADL. That is, only when an object is actually used, it is recognized that the activity is performed. For example, when a behavior of drinking water is desired to be recognized, an RFID tag is attached to a cup filled with water, and the cup is recognized by the reader manufactured in the shape of glove. Then, when a user takes a motion of drinking water, that is, he/she moves his/her arm up and down, it is recognized that the user is drinking water. As another example, when a screw driver is used, a recognized object is the screw driver. Further, when the hand of a user moves rotationally, it is recognized that the screw driver is actually used to fasten or unfasten a screw.

Figure 4:
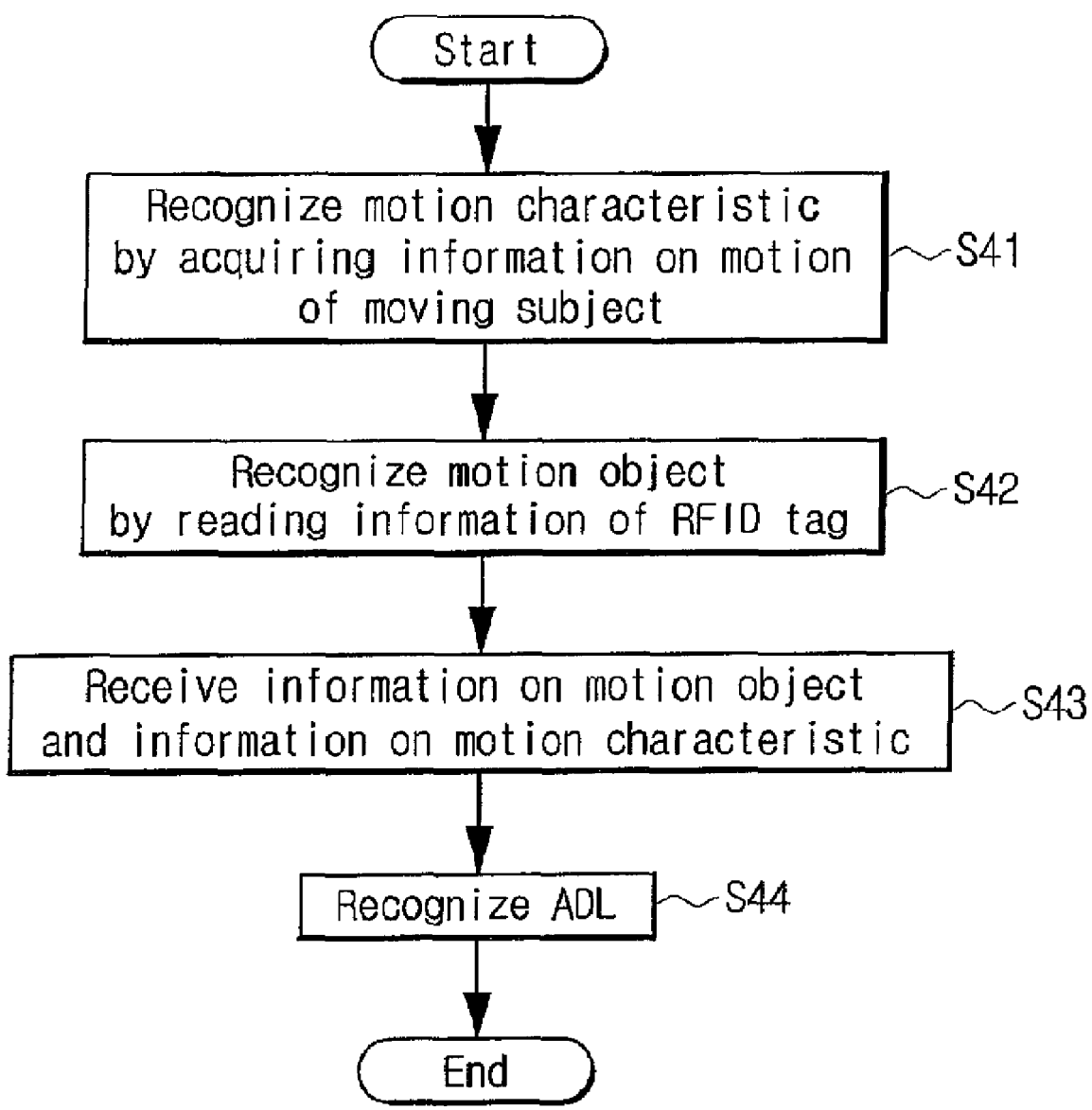
FIG. 4 is a flow chart showing a method for recognizing ADL according to an embodiment of the invention.

FIG. 4 is a flow chart showing a method for recognizing ADL according to an embodiment of the invention. As shown in FIG. 4, the method includes the steps of recognizing a motion characteristic by acquiring acceleration information on the motion of a moving subject (S41), recognizing a motion object by reading information of an RFID tag (S42), receiving information on the recognized motion characteristic and information on the moving subject (S43), to recognize ADL (S44).

The recognizing of the motion characteristic (step S41) includes the steps of: recognizing the current state of the body of the moving subject based on the motion characteristic information for the lower part of the body, and recognizing detailed motion characteristics based on the motion characteristic information for the upper part of the body of the moving subject. That is, the motion characteristic information for the lower part of the body is used to judge whether the moving subject stands, lies, sits, walks, or runs. Then, the detailed motion characteristic is recognized. For example, combing the hair while standing can be discriminated from combing the hair while sitting. The sequence of the steps needs not be limited. That is, after the current state of the body is recognized, the detailed motion characteristics may be recognized. Alternately, after the detailed motion characteristics are recognized, the current state of the body may be recognized.

The recognizing of the ADL (step S44) includes the steps of classifying the received motion characteristic information into predetermined motion type classes, and classifying the motion characteristic information as an ADL only when the relationship between the classified motion type classes and the motion object information is established. For example, the motion of the wrist is analyzed so as to be classified as a rotational motion class. When the motion object is recognized as a screw driver, the motion may be analyzed as a behavior of fastening or unfastening a screw in accordance with an essential property of the screw driver.

As for the classified motion type classes, an up-and-down motion, a down-and-up motion, a left-and-right motion, a right-and-left motion, a front-and-back motion, a back-and-front motion and a rotational motion are exemplified.

Figure 5:
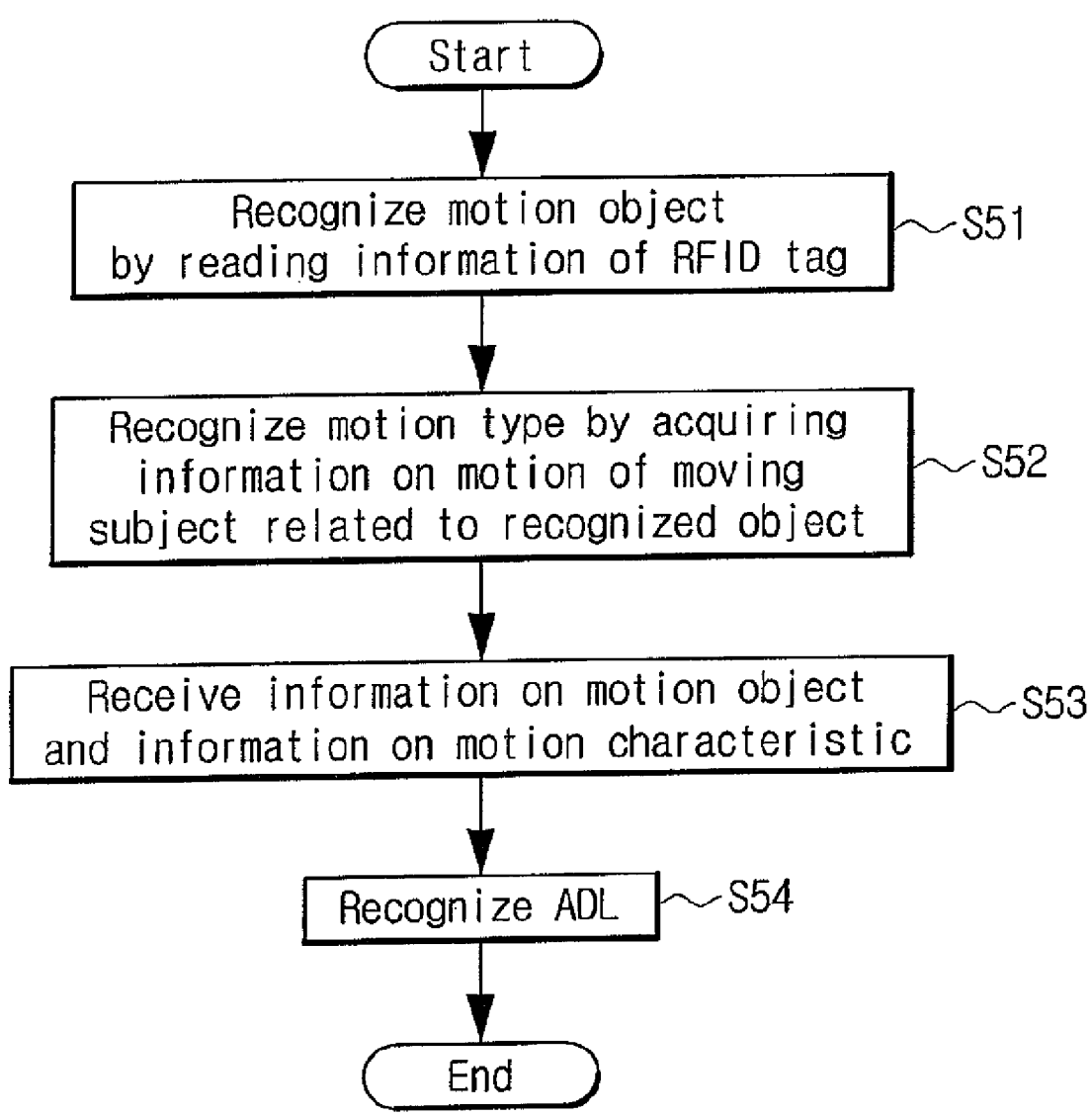
FIG. 5 is a flow chart showing a method for recognizing ADL according to another embodiment of the invention.

FIG. 5 is a flow chart showing a method for recognizing ADL according to another embodiment of the invention. As shown in FIG. 5, the method includes the steps of recognizing a motion object by reading the information of an RFID tag (S51), acquiring the motion information of the moving subject only when the motion coincides with an essential behavior of the recognized object (S52), receiving information on the recognized motion characteristic and information on the motion object (S53), to recognize ADL (S54).

In the method, the motion object is recognized, and the motion characteristic of the moving subject is analyzed and judged only when the motion coincides with an essential behavior of the recognized object. For example, when the motion object is a comb, it is judged whether the motion of the wrist is recognized or not. When the motion is recognized, it can be judged that the hair is combed. In this case, motion characteristics which have nothing to do with the motion object do not need to be analyzed.

Figure 6:
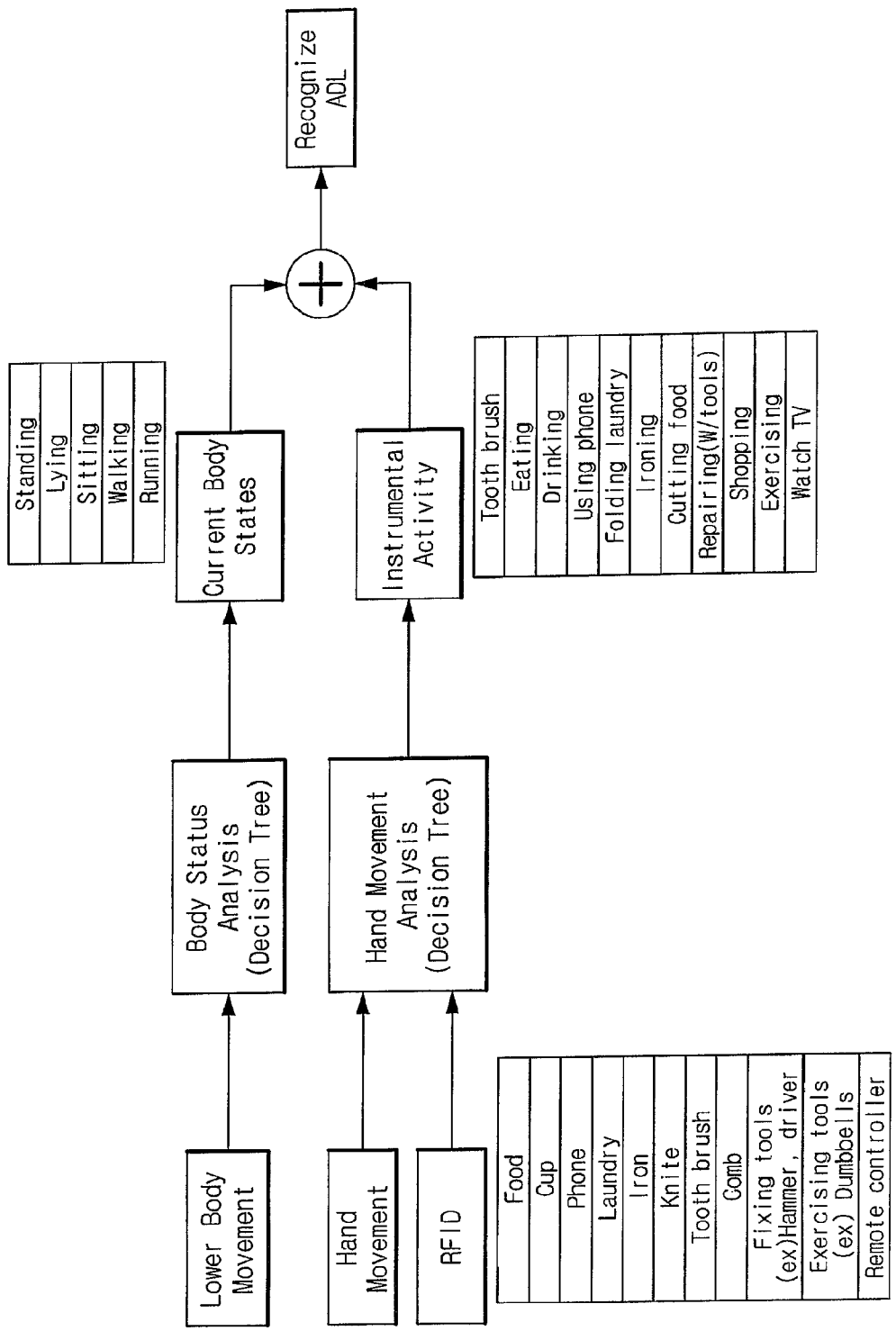
FIG. 6 is a diagram showing the overall system for recognizing ADL according to the invention.

FIG. 6 is a diagram showing the overall system for recognizing ADL according to the invention. Referring to FIG. 6, the motion information of the lower part of the body is acquired to analyze the state of the body, and the current state (standing, lying, sitting, walking, or running) of the body is recognized. Further, the motion information of the upper part of the body is acquired, and information on a motion object is acquired through an RFID tag. Then, the motion of the upper part of the body is analyzed to recognize an instrumental activity. The recognized body state and the instrumental activity are combined so as to recognize ADL.

According to the invention, the motion of a moving subject is accurately recognized, and an object of an instrument activity is accurately recognized, which makes it possible to increase the reliability of the recognizing ADL.

Further, since the ADL can be accurately classified, it is possible to monitor the state of a patient or whether an elderly person who lives alone can take care of himself/herself. Further, the apparatus of the invention can be used as a system for grasping the activities of members in a special group, for example in military training.

While the present invention has been described with reference to exemplary embodiments thereof, it will be understood by those skilled in the art that various changes and modifications in form and detail may be made therein without departing from the scope of the present invention as defined by the following claims.

What is claimed is:

1. An apparatus for identifying an activity of a moving subject, the apparatus comprising:
 a radio frequency identification (RFID) reader for identifying a motion object separate from the moving subject by reading an RFID tag attached to the motion object;
 a motion detector attached to the moving subject for identifying a motion characteristic of the moving subject by detecting acceleration of the moving subject; and
 a controller for identifying the activity of the moving subject based on an identity of the motion object received from the RFID reader and a type of motion of the moving subject, the controller configured to identify the activity by:
  classifying the motion characteristic received from the motion detector into a motion type in predetermined motion type classes; and
  recognizing the activity responsive to the classified motion type and the identified motion object satisfying a predetermined relationship.

2. The apparatus according to claim 1, wherein the motion type classes include an up-and-down motion, a down-and-up motion, a left-and-right motion, a right-and-left motion, a front-and-back motion, a back-and-front motion and a rotational motion.

3. The apparatus according to claim 1, wherein the controller recognizes the motion object based on the identity of the motion object received from the RFID reader, and recognizes the motion type that can be taken with the identified motion object.

4. A method for identifying an activity of a moving subject, the method comprising the steps of:
 identifying a characteristic of a motion by detecting acceleration of a moving subject, comprising:
  determining motion of a lower part of the moving subject; and
  determining motion of an upper part of the moving subject;
 identifying a motion object by reading information from an RFID tag attached to the motion object, the moving subject separate from the motion object; and
 identifying the activity of the moving subject based on the identified motion characteristic and the identified motion object, comprising:
  classifying the motion characteristic into a motion type in predetermined motion type classes; and
  recognizing the activity responsive to the classified motion type and the identified motion object satisfying a predetermined relationship.

5. The method according to claim 4, wherein the motion type classes include an up-and-down motion, a down-and-up motion, a left-and-right motion, a right-and-left motion, a front-and-back motion, a back-and-front motion, and a rotational motion.

* * * * *